United States Patent [19]

Nguyen et al.

[11] Patent Number: 4,914,289

[45] Date of Patent: Apr. 3, 1990

[54] ARTICLE INSPECTION SYSTEM FOR ANALYZING END AND ADJACENT SIDES

[75] Inventors: Cap V. Nguyen, Lantana; Tyce Fitzmorris, Lake Park; Eric Espenhahn, West Palm Beach, all of Fla.; Dale W. Kline, Hatfield, Pa.; Roger Chang, Fort Lauderdale, Fla.

[73] Assignee: Inex-Vistech Technologies Incorporated, Riveria Beach, Fla.

[21] Appl. No.: 262,885

[22] Filed: Oct. 26, 1988

[51] Int. Cl.[4] .............................................. G01N 9/04
[52] U.S. Cl. .................................. 250/223 B; 356/240
[58] Field of Search ................... 250/223 B; 356/240; 209/524, 526, 529; 358/106

[56] References Cited

U.S. PATENT DOCUMENTS

| | | | |
|---|---|---|---|
| 3,639,067 | 2/1972 | Stephens | 356/240 |
| 3,687,559 | 8/1972 | Fischer | 356/240 |
| 4,025,201 | 5/1977 | Deane | 356/240 |
| 4,026,414 | 5/1977 | Ellinger | 250/223 B |
| 4,262,196 | 4/1981 | Smith | 250/223 |
| 4,293,219 | 10/1981 | Ducloux | 356/240 |
| 4,424,441 | 1/1984 | Bieringer et al. | 250/223 |
| 4,435,641 | 3/1984 | Hajime | 250/223 |
| 4,448,526 | 5/1984 | Miyazawa | 356/237 |
| 4,454,542 | 6/1984 | Miyazawa | 250/223 B |
| 4,491,728 | 1/1985 | Fischer | 250/223 B |
| 4,498,003 | 2/1985 | Cibis | 250/223 |
| 4,546,247 | 10/1985 | Peyton et al. | 250/223 |
| 4,580,045 | 4/1986 | Kulig | 250/223 |
| 4,606,635 | 8/1986 | Miyazawa et al. | 356/240 |
| 4,650,326 | 3/1987 | Nagamine et al. | 356/240 |
| 4,680,463 | 7/1987 | Lutgendorf et al. | 250/223 B |
| 4,731,649 | 3/1987 | Chang et al. | 358/106 |
| 4,758,084 | 7/1988 | Tokumi et al. | 250/223 B |

FOREIGN PATENT DOCUMENTS

| | | | |
|---|---|---|---|
| 0025041 | 2/1986 | Japan | 250/223 B |
| 2042164 | 9/2980 | United Kingdom | |

*Primary Examiner*—David C. Nelms
*Assistant Examiner*—Michael Messinger
*Attorney, Agent, or Firm*—Steele, Gould & Fried

[57] ABSTRACT

An article inspection system especially useful for containers having threaded ends includes a video camera, digitizer and data processor operable to analyze a video image collected through a lens system. The lens system has several alternatives, in each case including a wide aspect object lens, wider than the end of the article being inspected, with a refracting and/or reflecting light ray path operable to produce a two dimensional image including both the end of the article and the sides of the article adjacent the end. The optics produce a distorted image in which the sides of the article appear folded upwardly into the two dimensional image such that a two dimensional data array adequately represents the image of the end and the adjacent sides.

24 Claims, 3 Drawing Sheets

ARTICLE INSPECTION SYSTEM FOR ANALYZING END AND ADJACENT SIDES

FIELD OF THE INVENTION

This invention relates to the field of article inspection systems, and in particular to an automated article inspection system using a video processor, especially applicable for inspecting at the same time the ends and threaded sides of glass and plastic containers.

PRIOR ART

Article inspection systems especially useful for containers such as bottles and the like are known in various forms, some including analysis of views in side elevation and others including analysis of views in plan view, i.e., endwise. In connection with viewing the ends, a problem is encountered in that portions of the structures at the end of a bottle or the like, which structures engage a crimped-on or thread-attachable cap on the container, are not fully visible when viewing the container axially from the end. Crimped-on caps are attached around a lip at the extreme end of the container; threadable caps are attached by relatively-thick threads. In either case the structures adjacent the axial end of the bottle block the view of the structures spaced from the axial end. Analysis thus conventionally requires end analysis and also side analysis from angularly spaced perspectives around the bottle.

Defects in the container end that could prevent proper sealing with the cap, or cause injury to a user of the container, may take the form of chips, cracks, dirt or the like. Defects may also occur during manufacture, e.g., gas bubbles, surface wrinkles, etc. The prior art has attempted to show up such defects for analysis by means of illumination which may be directed wholly or partly inwardly toward the container, however, the container is nevertheless viewed axially downwardly by video or similar image analyzers, such that it is necessary to produce a scattering of a light beam in order to locate a defect, especially a defect located axially below any radially protruding part of the container, such as its threads.

In connection with examination of threads, light is normally scattered in a characteristic manner by the threads. The threads are comparatively irregular structures as compared to the smooth toroidal lip adapted to receive a crimp top. Therefore, particularly in connection with threaded containers, it has been especially difficult to effectively inspect containers by automatic means in order to discriminate against those with defects in their threads. Defects are also difficult to detect in surfaces of cap-receiving toroidal lips oriented downwardly away from the end.

U.S. Pat. No. 4,731,649-Chang et al. discloses a lens-like reflector which extends downwardly over a container end to illuminate the end by inwardly-directed light that is scattered by defects. The scattered light, however, is detected by an axially-directed video camera.

United Kingdom Patent application No. 2,042,164-Ashcroft discloses an arrangement wherein a plurality of light detectors and complementary light receivers are mounted in a block having a plano-convex cross section (FIG. 3) that forms a concave shell over a container end. The block cannot function as a lens because it is opaque, being merely a mounting block for the light sources and receptors.

These references depend on scattering (uneven reflection and refraction) due to defects. This is a conventional means for discriminating good containers from bad containers. U.S. Pat. Nos. 4,650,326-Nagamine et al.; 3,639,067-Stephens; 4,546,247-Peyton et al.; 4,293,219-Ducloux; and, 4,498,003-Cibis all rely upon this basic idea of illuminating a container rim with a beam of light and sensing defects by sensing scattering of the beam in a manner that will be characteristic of defects but not smooth container lips.

In illuminating a container by means of light directed at least partly inwardly toward the container, it is possible to detect scattering of light by axially viewing the container. This procedure, which is not unlike use of discrete light sources and light receptors, is employed in U.S. Pat. Nos. 4,606,635-Miyazawa et al.; 4,435,641-Hajime; and, 4,262,196-Smith, in addition to the foregoing patent to Chang et al. In U.S. Pat. No. 3,687,559-Fischer, the reverse arrangement is employed, i.e., an axially-directed light source illuminates the container and scattering is detected by radially-directed discrete sensors.

In connection with illumination of a container, axially-directed video cameras or similar means involving a matrix of photo-detector elements upon which an image is focused, are disclosed in U.S. Pat. Nos. 4,448,526-Miyazawa; 4,580,046-Kulig; and, 4,424,441-Bieringer et al. In each case, it is possible with detectors of this type to produce a digital representation of an image including data representing dots or "pixels" (picture elements) which can be operated upon, compared and analyzed by means of a digital computer or the like, for example comparing the light intensity of adjacent pixels and thereby discriminating for defects which cause light scattering.

In U.S. Pat. No. 4,025,201-Deane, and in other patents, plural light sources and plural detectors are arranged wholly or partly to surround a container for locating sidewall defects. For example, a plurality of light sources such as video cameras or discrete detectors are angularly spaced around the side walls of a container in order to monitor for defects which may appear in angularly spaced locations, which locations are visible in side elevation. The object of a conventional system is to present a distortion-free set of elevation and plan views for analysis. This is accomplished via plural cameras or by reflectors producing plural separate undistorted views of the container. Although the effect of such devices is coverage around the container, the devices do not disclose the possibility of a single wholly or partly wrapped-around view, distorted deliberately to encompass the axial end of a container and, in the same view, the radial sides of the container adjacent the end.

None of the foregoing patents attempts to use an axial viewer such as a video camera for directly analyzing in one two-dimensional frame not only the axially-directed portions of a container, but also radially-directed portions adjacent the axial end.

According to the present invention, a distorted two dimensional view of the three dimensional container is presented to an axially-directed video camera through a lens or reflector optical system which has a wide enough object area to encompass not only the axial end of the container, but also the sides of the container adjacent the axial end. This in effect produces an image which in apparent effect spreads the sides of the container upwardly adjacent the end. The distorted view looks in part radially inwardly (or radially outwardly) through the threads, in one two dimensional axially directed view. This procedure departs substantially from conventional teachings in the prior art in that a deliberately distorted view is obtained in order to provide a two-dimensional array of data representing the three dimensional object, incorporating the end and at least so much of the sides of the container as encompass the threads or toroidal cap lip adjacent the end. The sides are normally oriented substantially perpendicular to a plane occupied by the end, but a wide enough object lens with adequate depth of field viewing the container can provide a distorted image of the end and the container lip or threads on the sides of the container, which make up a distorted plan view for analysis using an axially-directed viewing device such as a video camera and a computer. Portions of the container at the extreme fringes of the image, which may be so distorted by the optical elements producing the two dimensional image that they are not useful for analysis, are ignored. The two dimensional image is made wide enough that the less severe distortion produced in the image as necessary to produce a two dimensional view of the threads adjacent the end of the container does not prevent an appropriate analysis of the image. When spread out in this manner, the image of a container and threads is characterized by a circle representing the true axial view of the container, and spiraling lines representing the helical threads descending axially on the side walls of the container adjacent the end.

According to the invention, the distorted view of the container as so described can be produced by a number of different alternatives such as cone prisms, collimating lenses, mirror and lens combinations and the like. In each case, the image presented axially to a viewing apparatus is arranged to include not only the axially-presented portions, but also at least partly radially presented portions of the container. In this manner, the whole container end can be analyzed using a two dimensional image as produced by a video camera, which is fast and effective.

SUMMARY OF THE INVENTION

It is an object of the invention to produce a two dimensional image of at least part of a three dimensional container, which image is more easily analyzed than a plurality of axial and radial views of the container which might cover the same area.

It is another object of the invention to facilitate automated container inspection using a minimum of hardware and software.

It is yet another object of the invention to more effectively analyze threads of containers adapted to receive threadable caps.

It is yet another object of the invention to use distortion of an image to advantage such that the area covered thereby is maximized, while retaining the ability to analyze the distorted image for defects.

These and other objects are accomplished by an article inspection system especially useful for containers having threaded ends, including a video camera, digitizer and data processor operable to collect and analyze a video image through an optical system. The optical system has several alternatives embodiments, in each case including a wide aspect object field, wider than the axially-facing end of the article being inspected, the optical system defining refracting and/or reflecting light ray paths and being operable to produce a two dimensional image of the end of the article and sides of the article immediately adjacent the end. The optics produce a distorted image in which the inner or outer sides of the article are folded upwardly in the two dimensional image such that a two dimensional data array adequately represents the image of the end and adjacent sides.

BRIEF DESCRIPTION OF THE DRAWINGS

There are shown in the drawings the embodiments that are presently preferred. It should be understood, however, that the invention is not limited to the precise arrangements and combinations of particular features shown in the drawings, and is capable of other configurations and combinations in accordance with the claims appended hereto.

DETAILED DESCRIPTION OF THE PREFERRED EMBODIMENTS

Figure 1:
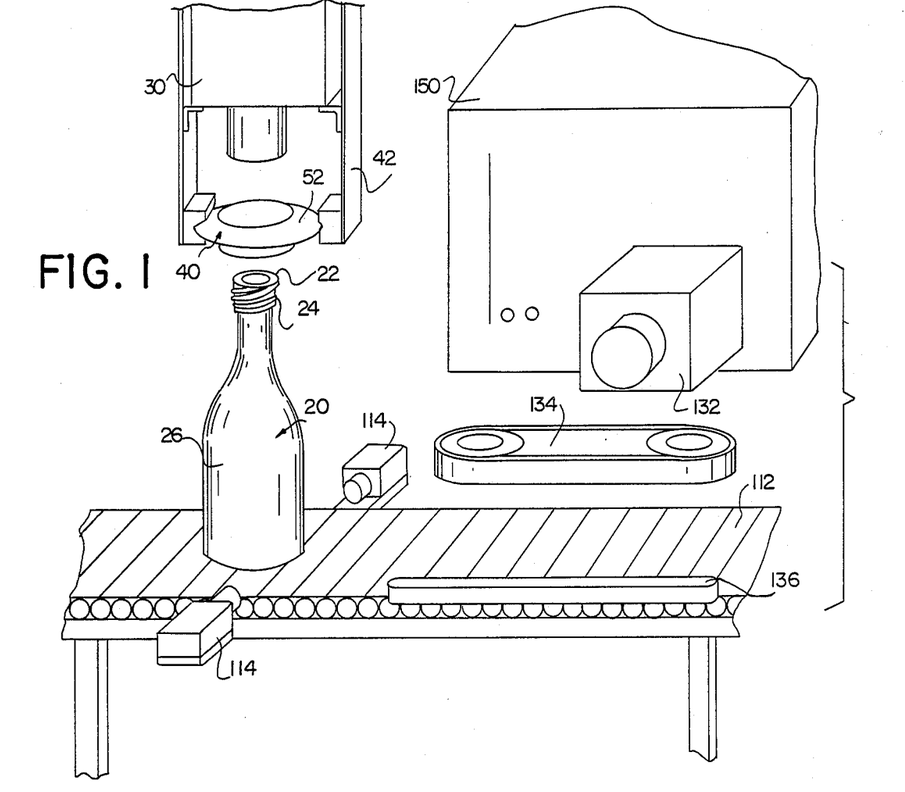
FIG. 1 is a perspective view of a container inspection system incorporating the invention.

A container inspection system including the container end inspection device according to the invention is shown in FIG. 1. Container 20 is carried along conveyor 112 to an inspection station including an axial inspection area in which video camera 30 is directed along a viewing axis toward container 20. The axial inspection device can be part of an overall inspection device including a side wall inspection area in which a side wall camera 132 is directed radially toward the container 20. One or more photocell/receptor pairs 114, 114 is provided along the conveyor 112, being positioned to define a detection line across the conveying path of the containers. The photocell/receptor pair 114, 114 produces a trigger signal ensuring repeatable container position when operating either or both of a strobe light and a synch signal connected to video camera 30 so as to capture an instantaneous image of the container via axially-directed video camera 30. The camera thereby collects an image looking downwardly toward lens system 40, as soon as container 20 is precisely correctly positioned in the field of view. Container 20 can be a crimp-cap type bottle (with a toroidal lip) or a threaded-cap type bottle (with a threaded end), or another container type, in any case having an end 22, occupying a substantially horizontal plane perpendicular to the viewing axis, and also substantially vertical or conically-sloping walls around the container adjacent end 22. In the bottle shown in FIG. 1, the container end is cylindrical and threads 24 are located on the sides adjacent end 22. Side walls 26 below the end, which can be examined downstream on the conveyor by means of side wall camera 132, can be sequentially exposed by spinning container 20 using an opposed spinning belt 134 and stationary pad 136, or alternatively a plurality of side wall cameras 132 or mirrors can be arranged at angularly displaced positions around container 20 in the side wall inspection area. This type of container inspection, unlike the invention, produces plural undistorted views for analysis.

The present invention seeks to provide a two dimensional image of container 20, which in addition to a view of the end 22, which is exposed by a simple axial view along container 20, also includes at least a part of the substantially vertical portions of container 20 which normally would be hidden or viewed at a very low angle of incidence, namely at least threads 24 adjacent end 22 and possibly portions of sidewalls 26 disposed farther down from the end 22.

The invention is described primarily with respect to containers having threads 24, which of course proceed in a helix downwardly from end 22 and progress around the axis of the container such that a cap (not shown) can be threaded on or off container 20 as desired. Threads are mentioned for analysis herein because the analysis of threads, which are relatively irregular as compared to simple toroidal lips for crimp-on caps, is quite demanding using typical inspection devices, normally requiring plural views and/or spinning the container. The invention is also applicable to analysis of geometrically-regular toroidal lips, as conventionally used to receive crimp caps, as well as to analysis of other shapes.

Figure 4A:
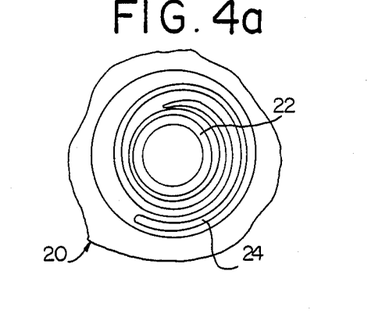
FIG. 4a is a representation of the image collected by the video camera according to the invention.
Figure 4B:
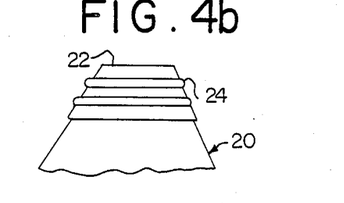
FIG. 4b is a fanciful side elevation suggesting how the container appears to be presented through the optical system of FIG. 6.

According to the invention, an optical system 40 is disposed between axial video camera 30 and container 20 to modify the image of the container presented to the video camera 30. In particular, optical system 40, carried on support 42 and including one or more lenses, refractors and/or reflectors, is arranged to define an object field which is effectively wider in a horizontal plane than the end 22 of container 20 and furthermore to define a plurality of obliquely converging or diverging light rays around the periphery of the object field, from video camera 30 to inner or outer sides of container 20 adjacent the end, which sides are thus shown axially. The two dimensional image viewed by video camera 30 includes not only the axially-directed horizontal portions of container 20 (and in particular the end 22 thereof), but also includes in the same frame a representation of the vertical portions, threads 24 and/or parts of side walls 26. This is achieved according to a number of alternative optical systems which for example view the thread area from outside the neck or from inside the neck, in each case producing a two dimensional image substantially as shown in FIG. 4a. The effect of the system, schematically shown in FIG. 4b (for the lens embodiment of FIG. 6, which views inwardly) and in FIG. 4c (for the reflector embodiment, of FIG. 5 which views outwardly), is to distort the view so as to make the end of container 20 appear very much like a conically tapering body instead of a substantially cylindrical one. The distortion of the image is beneficial because the inspection system is arranged to record and analyze particular features evident in the image of the end and immediately adjacent area (e.g., the threaded portions) shown more clearly as a result of the distortion.

The optical system 40 for revising the apparent image of container 20 is subject to embodiment in alternative ways, of which several are shown generally in FIGS. 2, 3, 5 and 6. The distorting optical systems may have refractors including one or more of plano-convex, biconvex, meniscus and conical prism lenses, and/or may use reflectors, for example an elliptical inward reflector for viewing through the neck from inside, in each case being operable to produce the necessary convergence of light rays to provide a focused two dimensional image. The light rays between video camera 30 and container 20 extend vertically from the camera, parallel to the viewing axis and one another, and at the optical system are arranged to converge. In this respect, the convex lenses are substantially of a collimating type, whereby parallel light rays from an infinitely distant light source bend (refract) upon entering and leaving the transparent glass or plastic lens material. The amount of bending depends on the index of refraction of air and the lens material, and on the angle of incidence of the light ray on the lens surface. When a ray passes from a less dense material (air) to a more dense material (glass or plastic), the ray is refracted at the surface to be oriented more closely toward a line normal to the surface between materials; and, when passing from a more dense to a less dense material the ray is refracted away from the line normal to the surface. By arranging rays oriented precisely parallel and vertical from the video camera toward the upper-most element in the lens array 40, to follow a path wherein the same rays are directed obliquely inwardly toward the container and, preferably are so directed that with regular spacing the rays proceed radially inwardly toward the container, the optical system produces a distorted two dimensional image of the three dimensional portion of the container which resides at the end and all around the end to show the threads adjacent the end.

The threads of course are cross-sectionally curving formations on the neck and therefore act as lenses to refract light passing through the neck from outside to inside. If illuminated from outside the neck, the threads appear from inside the neck as relatively brighter lines corresponding to the threads. Similarly, the threads from outside appear as relatively brighter lines due to reflection of incident light on the thread surfaces. In each case the lines are continuous if the threads are continuous. Damaged threads or missing areas are detectable as gaps in the bright lines.

Figure 3:
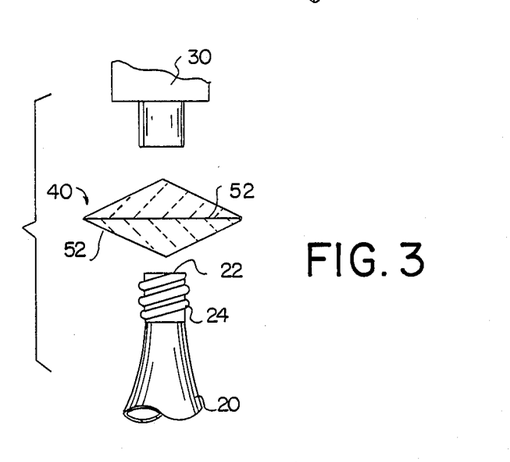
FIG. 3 is an alternative embodiment corresponding to FIG. 2.

One proposed means for producing a distorted two dimensional image in the manner contemplated is to provide a truncated conical lens or prism along the viewing axis as shown in FIG. 3. Light rays spaced farther radially from the viewing axis converge farther down the container neck, providing a view of the neck in the axial image of the container. The optical system can have one prism or two inverted prisms as shown, being wide enough to encompass not only the axial end but also the area adjacent the end, (e.g., 2.5 to 5.0 inches outside diameter). The prisms are conical at an angle of 25 to 40 degrees to horizontal. The axial center can be flattened (FIG. 1) or provided with a through hole. A lower angle is preferable to minimize light rays incident on the prism at an angle below the critical angle resulting in total reflection, but results in a larger prism.

As a result of the invention, the extreme end 22, which seals against the cap, as well as the threads, which mechanically force the cap downwardly onto the sealing surface, can both be inspected using a programmed image analyzer operative to analyze a two dimensional image.

The image analyzer can be programmed to "find" the container in the captured image even if the image is displaced from the center line of optical system 40. In that case the image can be analyzed by a simple convolution (contrast) analysis to find the center. An error of about 0.05 inches (0.13 cm) can be expected in typical handling systems, and the horizontal dimensions of the field of view of the optical system should be wide enough to encompass the container as well as this amount of error in each direction away from the container. Preferably, the container appears very near the center of the image due to triggering image capture very precisely. Moreover, the present image analysis technique does not rely on a non-distorted view. The pertinent features can be located in an asymmetrical, off-center image as well.

Figure 2:
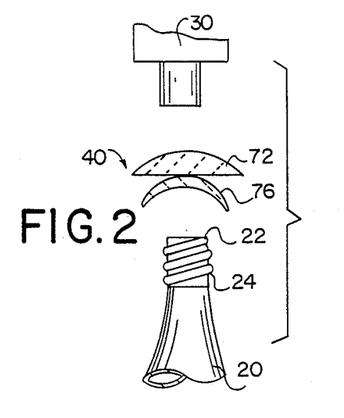
FIG. 2 is a side elevation view partly in section, showing a particular lens configuration in accordance with the invention.

Another means for altering the angle of convergence of the light rays and this control the field of view, is to control the slope and/or curvature of the lens dimensions. As shown in FIG. 3, a pair of oppositely-facing conical prisms can be employed. Steeper edges of such a prism arrangement more completely spread out the image of the threads. By choosing a curving collimating lens, for example a plano-convex or meniscus lens, some problems with focal length and internal reflections can be corrected. A series of lenses, such as the back-to-back conical prisms of FIG. 3 (possibly truncated to reduce internal reflections and the like at the unused axial central portion), or a series of plano-convex and meniscus lenses, produce a good image of the end and outside threaded walls adjacent the end at short overall focal length. FIG. 2 shows a plano-convex lens 72 and meniscus lens 76 in combination, and shows the passage of the refracted light rays proceeding between the video camera 30 and the container 20.

Figure 4C:
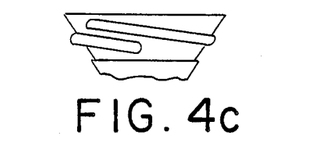
FIG. 4c is a side elevation comparable to FIG. 4b, but taken through the optical system of FIG. 5.
Figure 5:
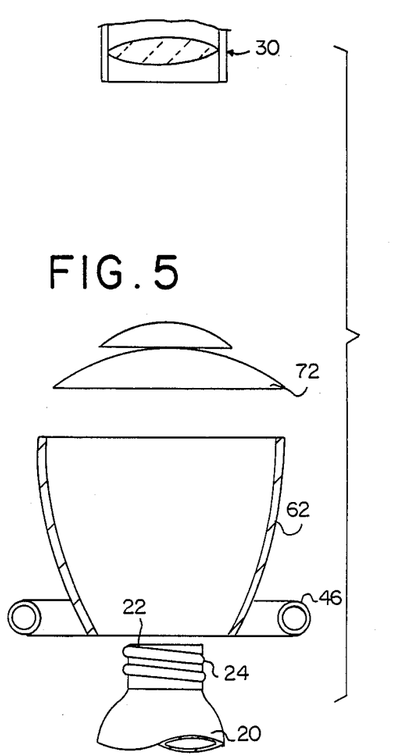
FIG. 5 is a partial section view showing an alternative embodiment using an elliptical reflector viewing the threads through the inner walls of the neck.

An improved optical system capable of producing the distortion shown in FIGS. 4a and 4c in a two dimensional image of the container is shown in FIG. 5. In this embodiment, an elliptical mirror 62, is placed between the container and the video camera. The container is illuminated from outside, for example via annular lamp 46. The fundamental property of an elliptical mirror is that a ray which passes through or originates from one focal point of the ellipsoid defined by the reflector surface must, after reflection, pass through the other focal point. In such a situation the two geometric foci are optical conjugate points, rendering the ellipsoidal surfaces free of any spherical aberration. Such a configuration shown in FIG. 5 results in rays from camera 30 being directed obliquely across the viewing axis against the inner walls of the neck. The relatively brighter lines produced by the lens effect of the thread shapes are visible on the inner walls. The image becomes reversed (i.e., right handed threads appear left handed) but the threads are clearly shown and readily inspected.

One or two plano-convex lenses can be inserted between the container and the reflector for magnifying the top sealing surface and shortening the focal length of the overall optical system. The reflector has, for example, a focal length of 10 to 20 mm, preferably 17.8 mm, the focal length of such reflectors being defined as the distance between the elliptical focus and the theoretical apex of the ellipse. The reflector provides a two dimensional image of the end 22 and the vertical walls adjacent threads 24, for analysis by the image processing equipment.

Figure 6:
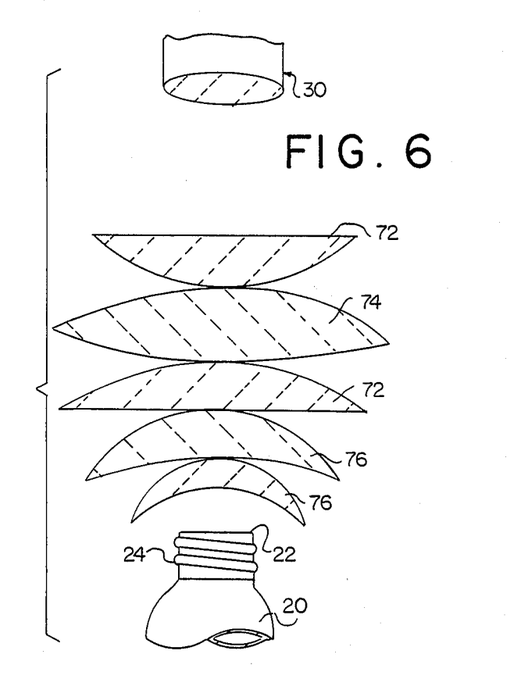
FIG. 6 is a section view showing an alternative optical path including a plurality of lenses placed serially along a viewing path, viewing the threads on the outer walls of the neck.

An alternative and more-extensive array of optical elements is shown in FIG. 6, together with a diagram illustrating passage of the light rays. In FIG. 6, a plano-convex, biconvex and meniscus combination lens system is shown, together with a tracing of the rays that proceed parallel to one another from the video camera through the lens system to a finally converging arrangement in which the light rays are directed both toward the end and the threads 24 of the container 20, in this case on the outside of the neck. A meniscus lens by definition has one convex surface and one concave surface. Such a lens is used in conjunction with other lenses to produce a system having an overall shorter focal length than with an alternative lens. Meniscus lenses are preferred because their shape adds no additional spherical aberration or coma effects which could detract from the quality of resolution in the image and the focal length is short. The analysis can be done monochromally, with colored filters and/or illumination, to avoid chromatic aberrations.

According to a preferred embodiment arranged as shown in FIG. 6, the lenses are plastic (M=1.517) and preferably have the following dimensional characteristics proceeding from camera 30 to container 20:

| Lens | Radius upper | Lower | Focal length | OD |
|---|---|---|---|---|
| camera lens (e.g.) | 3.721 cm | same | 50 mm | 5.0 cm |
| plano convex 72 | flat | 3.504 cm | 86.0 | 12.0 |
| biconvex 74 | 5.786 | 12.465 | 530.0 | 15.0 |
| plano convex 72 | 5.150 | flat | 65.4 | 14.0 |
| meniscus 76 | 2.697 | 5.493 | 260.0 | 11.5 |
| meniscus | 1.561 | 2.312 | 235.0 | 75 |

It will be appreciated that the character, dimensions and precise extent of divergence of the rays defined through the lens system 40 are subject to some variation. So long as originally parallel rays along the viewing axis from the video camera 30 eventually converge inwardly on the outside of the container 20 or diverge outwardly from inside the container, the effect is to spread out the image and to produce a two dimensional view of the end and adjacent sides even though the container is viewed directly axially through the center area of the lens system. In this manner, a top and partial side edge view is provided for analysis in one frame, with no need to rotate the container.

The image of the container, which is shown substantially in FIG. 4a, can be analyzed using various types of image processing equipment and techniques, including even manual inspection by a human. However, it is preferred that the two dimensional image be digitized by defining a plurality of picture elements (pixels) in the image, the intensity of light of each pixel or groups of adjacent pixels in an X-Y two dimensional array being encoded into digital data, the least significant bit of which represents the maximum resolution of intensity available on the system. Preferably, a one byte (8 bit) digital word produces adequate resolution, namely one part in 256 steps from maximum to minimum intensity.

According to digitizing and video encoding devices known in the art and useful herein, the video signal and the digitized representation thereof can be produced by a raster scanning technique or in parallel by a charge coupled device wherein the analog level of each charge coupled element in an XY array within camera 30 is shifted sequentially to an analog to digital converter, for conversion into digital format. The digital data words are stored in a digital memory array and can be addressed by a processor programmed to compare pixel intensities and detect any anomalies compared to the expected image. It is possible to normalize the pixel intensities based upon an overall average intensity (e.g., five adjacent pixels) in the image or upon a running average of a plurality of pixels in the image. Preferably, the differential intensity of each pixel in an array of selected pixels is compared to neighboring pixels by means of a convolution routine which defines and emphasizes edges in the image. The relative intensities of the pixels in groups are compared to expected positions for such edges as defined in the software driving the image processor. Preferably, a convolution representing a particular spacing and intensity pattern of pixels typically found across a good thread (for example: $-1$, $-2$, $+2$, $+2$, $+2$, $-2$, $-1$) is defined. This pattern matrix is multiplied against the matrix intensities of strings of adjacent pixels to calculate convolution sums applicable to the center pixels of the strings. The convolution pattern, for example, reflects a string of pixel intensities along a line perpendicular to a thread, i.e., from a pixel near the axial center along a radius segment (or "strip") proceeding outwardly. The convolution sums emphasize intensity patterns representing thread images and de-emphasize other patterns.

The screw thread inspection software preferably examines at least radial segments or strips crossing the screw thread of the bottle. The distorted image produced by the optics as described hereinabove produces a two dimensional image of the container, for example a soft drink bottle, beer bottle, or the like, which may be transparent, translucent or opaque, such that the vertical helically-threaded walls adjacent the top appear as spirals in two dimensions, the thread line spiralling outwardly from the center of top. The spiral typically proceeds outwardly 1.5 or 1.25 turns around the center of top 22.

Figures 10, 11, 12:
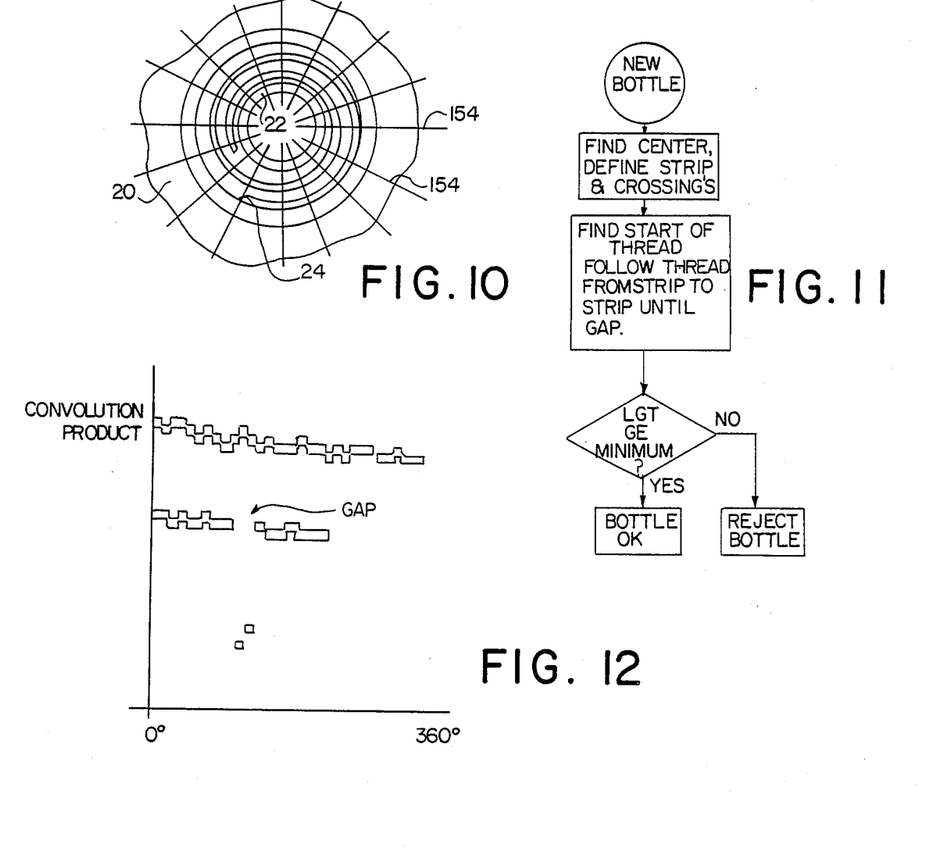
FIG. 10 is a two dimensional view of the image corresponding to FIG. 4, including segments of radii ("strips") defined by the image processor for use in a method of analysis.
FIG. 11 is a schematic flow diagram showing analysis of the image according to the invention.
FIG. 12 is a graph of convoluted intensity data along a radius segment or "strip".

The convolution products produce a data pattern graphed at FIG. 12. The thread spiral may become elongated if there is an error in centering between the axis of the optical system 40 and the axis of the container, but even then the graph will appear similar, if less linear, than shown in FIG. 12.

To trigger the collection of an image precisely with the arrival of the container at the precise geometric line of view, i.e. the axial center of the lens system, image collection occurs on a strobed basis triggered with arrival of the container. The precision of locating container 20 is achieved by use of a strobe light, or by causing camera 30 to collect a frame only after a trigger rather than on a free-running repetitive basis. It is also possible according to the invention and in connection with containers which are not moving extremely fast, to program the software to search the two dimensional pixel data and find the center of the container by locating edges in the image rather than to require extreme accuracy in the container positioning and extremely accurate timing in capture of the video image. The center of the image can be found by locating the horizontal and vertical positions of the extremes of the internal opening in the end 22 and averaging the extremes to find the center. By using photocell pair 114 for triggering, that the container will always be within a certain window in the image.

Once the apparent center of the end 22, and thus the center of the spiral of the threads is located, a plurality of radial strips are defined proceeding outwardly from the center and intersecting the threads. The strips defined lie perpendicular to the threads at each point they cross the threads. This is substantially true even if the container is slightly off the center of the optical system and therefore does not appear precisely round and symmetrical in the distorted image. The intensities of the pixels on each strip are noted in memory. The strips may be several pixels wide, for example five pixels.

The sealing end 22 and threads 24 on the container 20 appear as a succession of varying peaks of brighter and darker areas in the image, the threads being arranged spirally around the center. Although brightness peaks are usually threads in the bottle, they sometimes are due to reflections which can be identified due to characteristic features such as location or brightness "signature" and treated as noise. Noise and undependable data are filtered out in the image processing by multiplying the intensity data for pixels and their neighboring pixels by a convolution pattern of expected intensity for a typical good thread, emphasizing the image being sought and clearly pointing out any strips where the expected image is not found. The value of the convolution product for points along the strip is saved and compared to an expected pattern of intensity. This produces data as shown in the graph of FIG. 12, wherein the graphed points show the values of the convolution at strips along the threads. The threads should be continuous. When a stepwise change in the convolution product occurs in the graph of pixel data, this is interpreted as a gap or other defect (e.g., a chip).

The convolution technique, sometimes called an edge operator, can be arranged in hardware or in software to locate features such as threads appearing in the image by emphasizing patterns characteristic thereof.

The graphed points in FIG. 12 represent crossing of the radial strips over the threads. Having found these crossings and assuming the container has passed any other requirements of the analysis to this point (e.g., being adequately centered, having an expected range of pixel intensities, etc.), the next step is preferably to identify the extreme radially innermost (or outermost point) where the threads start along the angular spiral progression around the container and then ensure that the threads are continuous up to the other extreme. The end of the spiral, for example at the axial top of the threads, is found by checking the number of threads found to cross each radial strip progressing angularly clockwise or counterclockwise. By locating the transition from one thread per strip to two threads per strip, or between two threads and three, and so forth, the thread start and/or end are located.

Figure 7:
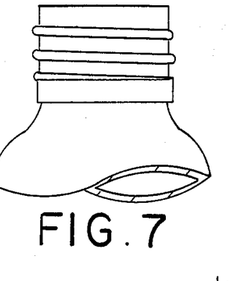
FIG. 7 is an elevation view of a perfect threaded container end.
Figure 8:
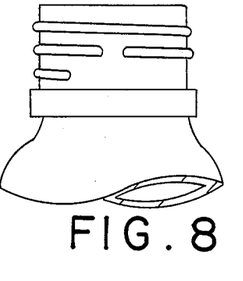
FIGS. 8 (showing a thread chip) and 9 (showing a thread chew) are elevation views corresponding to FIG. 7, showing examples of defective threads.
Figure 9:
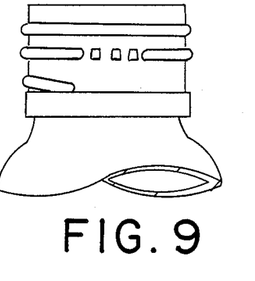

A good container is shown in FIG. 7 and containers with defective threads are shown in FIGS. 8 and 9. The analyzed image appears as in FIGS. 4a and 10, with the analysis proceeding as shown in FIG. 11. Having found the start of the thread and proceeding in a spiral from radial strip to radial strip around the bottle, the convolution peaks are compared. If the peaks are nearly equal, the thread is continuous. If the convolution peaks vary outside a predetermined amount (depending on the convolution) a discontinuity has been located. Some variation will occur even with good threads. For example, a centering error produces a periodic variation due to the distortion of the spiral thread image. Analysis continues from strip to strip around the image. If a strip is found which does not follow the continuous intensity pattern as shown in FIG. 12, this possible "hole" is either a defect in the thread (FIG. 8) or the end of the thread. These two conditions can be distinguished by determining how far the analysis progressed from strip to strip (e.g., 42 of 48 strips in FIG. 12) before the discontinuity was located.

When an edge or hole is found while progressing along the threads from radius crossing to radius crossing, the total length of the thread to that point is compared to the minimum required length. If the hole was found before the minimum length (e.g., 45 strips in the example) was reached, the bottle is defective. The minimum is substantially equal to the length of a full thread.

According to the presently preferred embodiment, at least 32 strips are defined around the end, each crossing one or two threads producing pronounced peaks in the convolution product, the value of which peaks should be roughly continuous from strip to strip. Similar techniques can be used as to other features, e.g., to ensure that there is an adequate top finish area (i.e., an unthreaded area located axially above the start of threads) or an adequate collar below the threaded area). Unexpected variations in intensity are interpreted as chips, flats, deformities or the like, and the container is rejected.

Using available image processors and the analysis technique as described above, the system of the invention is able to detect a chipped thread as small as 0.6 mm in a thread. The inspection criteria for threads can also be combined with typical video inspection criteria for containers generally, e.g., sidewall analysis wherein any variation in intensity between adjacent pixels (i.e., an edge) of greater than a predetermined amount, or wherein an excessive number of small (individually acceptable) variations, will also result in rejection of the container.

It is possible to ensure correct operation of the system by monitoring for the number of rejections or defects and disabling operation if the number of rejects or detected faults exceeds what can be reasonably expected from the system in connection with typical containers applied thereto. Therefore, the system can be arranged to shut down or to pass all containers (and sound an alarm) if so many containers appear rejectable that the operational condition of the system is suspect. Detection accuracy will vary somewhat with whether the container is opaque, translucent or clear. Detection accuracy is best with a clear container due to the relatively greater variations in intensity which are produced by defects and also by nominal features. Intensity variations are detectable due to surface damage and also those which are caused by deficiencies in the glass composition such as bubbles, perpendicular or horizontal lines, wrinkles, stratifications and the like, and by noticeable damage, especially scuffing. Similarly, bottles having a height out of acceptable tolerance will produce a poor image in the system and therefore are generally interpreted as defective.

An image inspection system of the disclosed type can inspect 400 containers per minute, or up to 850 containers per minute with high performance video processing and highly accurate container positioning features. Clear or translucent containers (e.g., white, green and brown) are all subject to analysis, in sizes commercially available, typically 7 ozs. to 1 liter. A job change on a production line for making, washing, filling or the like, from one type of container to another, can be accomplished promptly by switch inputs to the image processing computer, if necessary including re-positioning the height of the optical system and video camera for the new size. The optics and/or camera can be mounted as a unit on common supports as shown in FIG. 1, whereby job changes including substitution of optical systems can be accomplished in only a few minutes without difficulty.

By employing a large enough object dimension on the optical system, the diameter of the edge area can be anywhere within a moderately large span, typical sizes being for example from 1 inch (2.5 cm) up to 1.75 inch (4.5 cm). With an object lens large enough for the largest container, job changes can be made entirely in programming, i.e., without the need for changing optical devices. Alternatively, the optical systems can be specific to the particular containers and replaced by quick-change fittings when changing jobs.

The invention as so disclosed is a method for inspecting successive articles such as containers 20, each having an end 22 and sides 24 adjacent the end 22, comprising the steps of placing the article 20 at an inspection station having an optical system 40 directed toward the end 22, and defining light rays directed obliquely inwardly toward the sides 24, collecting with the optical system 40 a dimensional image 32 (FIGS. 4a and 4b) of the end 22 and the sides 24, said image 32 being a distorted view of the end 22 and sides 24 wherein the sides 24 appear folded up adjacent the end 22, either inwardly or outwardly, and discriminating among the articles 20 based upon features 36, 38 appearing in the two dimensional image 32.

Preferably the image is enhanced to emphasize certain features 24 therein. The method can include collecting a video signal representing the image 32 and wherein the discriminating step is automatically conducted using a processor 150 operable to analyze the video signal.

The video signal can be digitized to provide a plurality of pixels in the image 32, the pixels having defined intensities, and wherein the processor is a digital computer 150 programmed to compare the intensities to accomplish the discriminating step.

The collecting step using the optical system preferably includes projecting the image 32 through a lens array 40 having at least one refracting lens 72, 74, 76 operable to define converging light rays directed at the sides 24 and light rays at least partly parallel to the line of view directed at the end 22.

The light rays can be projected to obtain said image through a lens array 40 including optical elements selected from the group conical prisms 52, elliptical mirrors 62, plano-convex lenses 72, biconvex lenses 74 and meniscus lenses 76.

The discriminating step can include the steps of finding a predetermined point on the end 22 defining radial segments or strips 154 emanating radially from the predetermined point and locating features 24 of the article 20 appearing along said strips 154, and, comparing at least one of a position and an intensity of said features relative to the strips to an expected position and intensity.

The article being inspected can be a container having an opening at the end 22 and structures 24 on the sides for attaching a cover to the end 22, the discriminating steps selecting for containers 20 with damage to at least one of the end 22 and the structures 24. The container can be a light transmissive container and the structures can be threads, discriminated for chips, chews and like gaps. Preferably, a plurality of successive containers are inspected in sequence, being placed at the inspection station by a transport conveyor operable to deliver successive articles to the inspection station.

The invention as so defined includes an inspection system for examining both an end 22 of articles 20 and sides 24 of the articles 20 adjacent the end 22, the sides 24 being disposed at an angle relative to the end, for example perpendicular, the inspection system comprising means 112, 114 for locating the article at an inspection station, an optical system 40 directed toward the end 22, operable to collect an image 32 of the article 20 in two dimensions, the optical system 40 defining light rays directed toward the end 22 and obliquely inwardly towards the sides 24, either from outside or inside, whereby said image 32 of the article 20 in two dimensions is a distorted view of the article 20 including indicia respecting both the end 22 and the sides 24 in a two dimensional presentation, and, means 150 for discriminating for articles 20 based upon at least one attribute 36, 38, included in the image 32.

The system can include means illuminating the articles from outside, a video camera 30 and a digitizer operable to collect the image 32 of the article 20 through the optical system 40 in a two dimensional array of digital data. The means for discriminating for articles 20 is preferably a data processor 150.

The data processor 150 is operable to locate indicia in the image representing threads 24 on the sides and to discriminate among the articles 20 based at least upon continuity of the threads 24 and presence of contrasting portions in the image.

The optical system 40 can include a collimating lens configuration, the end and the sides of the article being effectively placed closer than a focal point of the collimating lens configuration.

The optical system 40 can include an elliptical mirror 62 for inspection from inside the article and/or a lens system, for example with at least one plano-convex lens 72.

The lens system can also include a serially-positioned succession of lenses including plano-convex, biconvex and meniscus lenses for inspection from outside the article. A conveyor 112 is preferably operable to deliver the successive articles 20 to the inspection station.

Whereas the invention has been disclosed together with embodiments illustrating its structures and functions, further embodiments and variations will now be apparent to persons skilled in the art. Reference should be made to the appended claims in order to assess the true scope of the invention claimed.

We claim:

1. A method for inspecting successive articles, each having an end and sides adjacent the end, comprising the steps of:
    placing the article at an inspection station having an optical system directed toward the end, the optical system producing a focused image wherein each point viewed on the article is focused to a corresponding point in the focused image, the optical system defining a line of view toward the end, and defining light rays directed obliquely toward the side, each focused to a point in said image;
    collecting with the optical system a two dimensional image of the end of the end and the sides, said image being a focused but spatially distorted view of the end and the sides wherein the sides appear folded up adjacent the end; and,
    discriminating among the articles by recognizing features appearing in the two dimensional image.

2. The method of claim 1, further comprising enhancing the image to emphasize features therein.

3. The method for inspecting articles of claim 1, further comprising collecting a video signal representing the image and wherein the discriminating step is automatically conducted using a processor operable to analyze the video signal.

4. The method for inspecting articles of claim 3, further comprising digitizing the video signal to define a plurality of pixels in the image, the pixels having defined intensities, and wherein the processor is a digital computer programmed to compare the intensities to accomplish the discriminating step.

5. The method for inspecting articles of claim 1, wherein the collecting step using the optical system includes projecting the image through a lens array having at least one refracting lens operable to define light rays directed at the sides from outside the container.

6. The method for inspecting of claim 1, wherein the collecting step includes reflecting the image through a reflector operable to define converging light rays directed at the sides from inside the container.

7. The method for inspecting articles of claim 6, further comprising illuminating the container from outside.

8. The method for inspecting articles of claim 1, including projecting said image through an optical system including optical elements selected from the group: elliptical mirrors, plano-convex lenses, biconvex lenses and meniscus lenses.

9. The method of claim 3, wherein the discriminating step includes the steps of:
    finding a predetermined point on the end;
    defining radial strips emanating from the predetermined point and sensing features of the article appearing along said strips; and,
    comparing at least one of a position and an intensity of said features to an expected position and intensity.

10. The method for inspecting articles of claim 9, wherein the article is a container having an opening at the end and structures on the sides for attaching a cover to the end, the discriminating step selecting for containers with damage to one of the end and the structures.

11. The method for inspecting articles of claim 10, wherein the container is a light transmissive container and the structures are threads.

12. The method for inspecting articles of claim 11, wherein the threads are discriminated for chips and chews.

13. The method of claim 1, comprising inspecting a plurality of successive articles in sequence, said placing being accomplished by a transport conveyor operable to deliver successive articles to the inspection station.

14. An inspection system for examining both an end of successive articles and sides of the articles adjacent the end, the inspection system comprising:
   means for locating each said article at an inspection station;
   an optical system directed toward the end, the optical system being operable to collect a focused two dimensional image of the article wherein each point viewed on the article is focused to a corresponding point in the image, the optical system defining light rays directed toward the end and toward the sides, whereby said image of the article in two dimensions is a focused view of the article, spatially distorted to include both the end and the sides in two dimensional presentation; and,
   means for discriminating the successive articles based upon at least one attribute of the articles included in the image.

15. The inspection system of claim 14, further comprising means for enhancing said at least one attribute by emphasizing a pattern characteristic thereof.

16. The inspection system of claim 14, further comprising a video camera and a digitizer operable to collect the image of the article through the optical system in a two dimensional array of digital data and wherein the means for discriminating for articles is a data processor.

17. The inspection system of claim 16, wherein the data processor is operable to locate indicia in the image representing threads on the sides and to discriminate among the articles based at least upon continuity of the threads.

18. The inspection system of claim 16, wherein the optical system in part defines a lens configuration, directing light rays from the video camera outwardly toward the sides.

19. The inspection system of claim 18, wherein the light rays are directed inwardly toward the sides from outside the container.

20. The inspection system of claim 18, wherein the light rays are directed inwardly toward the sides from inside the container.

21. The inspection system of claim 20, further comprising illumination means disposed in an annular pattern outside the container.

22. The inspection system of claim 16, wherein the optical system includes an elliptical mirror shaped and positioned relative to the article such that said light rays originating at points on the article, passing through a focal point of an ellipsoid defined by a surface of the elliptical mirror, after reflection on the elliptical mirror pass through a second focal point of the elliptical mirror, and further comprising a lens disposed at the second focal point for collecting the image and focusing the image in two dimensions.

23. The inspection system of claim 16, wherein the lens system includes a plano convex lens, a biconvex lens and a meniscus lens positioned serially between the article and a video camera, the video camera having an object lens and the lens system being operable to converge the light rays at the object lens, whereby the video camera focuses the image obtained from the lens system.

24. The inspection system of claim 17, further comprising a conveyor operable to deliver successive articles to the inspection station.

* * * * *